(12) United States Patent
Filo

(10) Patent No.: US 9,398,745 B2
(45) Date of Patent: Jul. 26, 2016

(54) ORGANIC COMPOSITION FOR PROTECTION OF CROPS AGAINST BLACK FROST AND THE METHOD FOR ITS APPLICATION

(71) Applicant: Diego Fernando Filo, Ezeiza (AR)

(72) Inventor: Diego Fernando Filo, Ezeiza (AR)

( * ) Notice: Subject to any disclaimer, the term of this patent is extended or adjusted under 35 U.S.C. 154(b) by 135 days.

(21) Appl. No.: 14/199,587

(22) Filed: Mar. 6, 2014

(65) Prior Publication Data

US 2015/0250109 A1 Sep. 10, 2015

(51) Int. Cl.
*A01G 13/06* (2006.01)
*A01G 13/00* (2006.01)
*A01N 31/02* (2006.01)

(52) U.S. Cl.
CPC .............. *A01G 13/065* (2013.01); *A01G 13/00* (2013.01); *A01N 31/02* (2013.01)

(58) Field of Classification Search
CPC ..... A01G 13/00; A01G 13/065; G01C 21/26; G01C 21/367; G06F 17/30241
USPC ................................................ 42/2; 514/738
See application file for complete search history.

(56) References Cited

U.S. PATENT DOCUMENTS

| 3,045,394 A | * | 7/1962 | Coulter ................ A01G 13/065 427/4 |
| 2009/0085003 A1 | * | 4/2009 | Tochigi .................... C09K 3/18 252/70 |
| 2011/0033532 A1 | * | 2/2011 | Angel .................. A61K 9/2018 424/465 |

OTHER PUBLICATIONS

The definition of "include", Merriam-Webster [online]. [retrieved on Sep. 15, 2015]. Retrieved from: http://www.merriam-webster.com/dictionary/include.*

* cited by examiner

*Primary Examiner* — Janet Epps-Smith
*Assistant Examiner* — Courtney Brown
(74) *Attorney, Agent, or Firm* — Defillo & Associates, Inc; Evelyn A. Defillo

(57) ABSTRACT

The present invention is an organic composition for the protection of crops against black frost and the method for its application over the crops. The novelty of this invention consists not only in the composition of the product itself, but also in the calculation of the percentages of the organic components that intervene in the product; and, in the determination of the moment when the product must be applied over the crops. This invention is a very simple composition where the calculation of the percentages of the two main components is obtained by multiplying the "Filo Index" (real humidity and temperature/historical values of humidity and temperature for the area) by the component; and, the percentage of the second component is calculated by subtracting the first result from 100.

3 Claims, 3 Drawing Sheets

ORGANIC COMPOSITION FOR PROTECTION OF CROPS AGAINST BLACK FROST AND THE METHOD FOR ITS APPLICATION

FIELD OF THE INVENTION

The present invention is an organic composition for the protection of crops against black frost and the method for its application.

The novelty of the invention consists not only in the composition of the product, but also in the calculation of the percentages of the organic components involved in its production and the time at which the composition should be applied over the crops.

The composition is a combination of alcohols with glycols, a bactericide, a fungicide, and a colorant.

The calculation of the percentage of the two main components of the product is achieved by using an index obtained from the humidity values and real temperature of the last 15 days versus the historical values of humidity and temperature of the zone. This value is multiplied by 50% of one of the components, obtaining the value of the % of that component in the composition.

To obtain the percentage of the second component, the value obtained for component 1 is subtracted from 100.

The best crop protection is obtained when the product is applied 7 to 30 days prior to frost, in order to ensure that the dew point occurs above 0 degrees Celsius. In order to achieve this result, it is necessary to modify the humidity creating the conditions to make this happen.

PRIOR ART

The present invention is an organic composition for the protection of crops against black frost and the method for its application. The novelty of this invention consists not only in the composition, but also in the calculation of the percentages of the organic components involved in the composition and the time at which it should be applied over the crops.

Knowing that frost is a meteorological phenomenon that occurs when the temperature of the air mass next to the ground drops below 0° C.

In the case of black frost, the phenomenon occurs during the night due to the heat loss from the soil that is radiated into the atmosphere where the heat leakage is favored by the low humidity of the air, cloudless skies, and absence of wind. When these conditions occur, vegetable tissues suffer very severe burns that give plants a blackish appearance.

Within the numerous methods found in the prior art to confront frost, can be found:

Passive protection methods that use indirect measures to reduce frost damage such as the choice of planting time or choosing species that are more resistant or tolerable to low temperatures. Another form is the use of forest type trees such as pines or cypress trees, or ornamentals such as palm trees, in order to create a canopy over the crops, preventing the action of cold winds on the crops. Other methods include not plowing the soil; and covering the crops with insulating materials such as polyurethane, fiberglass or insulation materials containing water.

b) Active protection methods that use active measures to reduce frost damage. Irrigation, for example, is a method that tries to change the conditions of the environment. In this method, there are two ways of acting. One of them is having installed automated irrigation systems, or going personally to the field and irrigate abundant water over the crops susceptible to frost. Abundant watering produces a temperature around the soil and maintains it favorable, and also increasing the thermal conductivity of the ground, the evaporation, and the heat capacity of the soil. Water applied when the air temperature is 0 degrees Celsius or lower forms a film on the leaves or the branches that will have a temperature above 0° C. (water and ice at the same time), because the content of water vapor increases with respect to the original condition prior to irrigation. This method therefore enhances the risk of crop diseases.

Another active protection method is to heat the soil or the environment with different fuels. This method can be very expensive and not environmentally friendly.

In addition, fans are used in order to project hot air or a helicopter that prevents the concentration of low temperature air around the crops. This method is often used for high-performance and large area crops. Smoke is also commonly used, but it is not effective. The hot air of the smoke ascends to high altitudes where it loses all its heat, and does not prevent heat from escaping by radiation. In addition, the following day, if there is still smoke buildup in the environment, this will prevent the entry of sunlight (heat) and it will affect the crops.

In summary, the described methods are effective in the long run. On the one hand, irrigation is inexpensive and results are acceptable; while on the other hand, the use of heaters or fans is more effective but the high cost must be evaluated in order to prove its economic feasibility.

There are numerous patented compositions that affect or change the freezing point of plant tissue in order to protect crops from the effects of low temperatures. Amongst these we find Spanish Patent No. ES199509 that consists of a zinc composition that creates an artificial turbidity in the air as a means of protecting crops against frost. U.S. Pat. No. 5,133,891 held by Barr and Col, prevents frost through a composition of aluminum tris-[o-ethyl phosphonate] (fosetyl-Al) in the form of a wettable powder. Another document that is within the prior art is U.S. Pat. No. 8,562,854, held by Chauhan et al., dated Oct. 22, 2013, that claims a non-toxic de-icing/anti-freeze fluid which includes at least 20% by weight of a freezing-point depressant selected from short-chain polyols of 3-5 carbon atoms. The fluid also includes other components and is used to remove ice, frost, and snow from surfaces and/or to prevent the formation of ice on surfaces. This invention refers to the formulation of ecology, non-newtonian fluids, mainly for de-icing/antifreeze of aircrafts, as required by Society of Automotive Engineers Aerospace Materials Specification (SAE/AMS) 1428. The de-icing/anti-freeze fluid claimed in this patent presents a composition very similar to an invention of mine presented in Argentina on Jan. 6, 2010, entitled "Composition to Protect Crops from Extreme Temperatures of Maximum or Minimum", Act No. P20100100013. This invention was published on Mar. 23, 2011 and numbered AR075324 A1. The composition of this prior invention is glycol, benzoic acid, a dye, methylparaben, propylparaben and water, and the practical applications of my previous invention are very different. The differences between my previous invention AR075324 A1 and the present invention are mainly the methodology used to calculate the optimal percentages of the main components of the composition, the optimal time for the application to the crops, and the composition.

For the calculation of the percentages, I have developed an index that I will call the "Filo Index" which is calculated as the relationship between the average humidity and temperature of the last 15 days and the historical value of the humidity and temperature for the area where the product is to be applied.

As can be seen, none of the methods of the prior art are similar to the methodology claimed in this invention since it is a composition that acts on the balance between the humidity of the environment and that of the plant, establishing outside the tissues of the plants the necessary condensation so that freezing occurs without intracellular damage to the plant.

The composition of the present invention acts by taking water from the environment or the plant so that the dew point occurs above 0° C. The method produces, through its formulation and in its application, a humidity equilibrium between the plant and the environment that causes the freezing (frost) to occur outside the plant tissues, avoiding the freezing to occur before the condensation that would result in the freezing of the water contained in the plant tissues with the corresponding damage to these cells.

As discussed, there are many products in the prior art, however, all of these differ from the present invention in the composition and, above all, in the calculation of the Filo Index used to obtain the optimal percentages of the composition and the calculation of the time at which the product should be applied in order to achieve the balance between humidity and the dew point.

The closest prior art was compared with the present invention and noted that the present invention has differences in the inventive activity, which is novel and has industrial applications.

Therefore, both the composition of the product and the method of its application are claimed in the present invention, since neither of them acting separately could achieve the desired result. Therefore, in my opinion, both can be regarded as a new invention.

DESCRIPTION OF THE INVENTION

Figure 1:
FIG. 1 shows the application of the composition by means of a spray hose. INTA-EEA Alto Valle, September 2012.
Figure 1:

The organic composition for protection of crops against black frost and the method for its application, comprises not only in the composition but also in the calculation of the percentages of the organic components involved in the product and the moment when it should be applied.

The present invention represents a revolutionary way to confront what is a farmer's worse fear, because so far there are no crops that can survive black frost, even the most resistant species. When black frost occurs, frost does not form on the surface of the plant, that would act as an anti-freeze, but the cold and persistent air directly attacks the internal structure of the cells and crystals appear at the cell level that tore the internal membrane of the cells, and the internal membranes are dried out as a result of the freezing process. The result is the necrosis of the damaged tissues that suddenly turns black as a consequence of rotting. Many times, black frost will damage vital structures of the crops such as the trunk and the leaves, and the plant will die.

Frosts are meteorological phenomena that occur when the temperature of the air mass next to the ground falls below 0° C. Black frost occurs when the air temperature falls below zero degrees and no frost protection is formed on the surface of the plants. This phenomenon is a farmer's worse fear since there are no crops that can survive it, even the most resistant species. The dreaded black frost is a meteorological phenomenon that occurs in conditions of very low environmental temperature and humidity.

As previously indicated, the novelty of the present invention is not only in the composition of the product, but also in the calculation of the percentages of the organic components involved in the mixture and the time when the product should be applied over the crops.

The organic composition for protection of crops against black frost, and the method for its application of the present invention, is a very simple composition where the calculation of the percentage of each of the two main components is obtained by multiplying the "Filo Index" (current humidity and temperature/historical humidity and temperature values in the area) times the component. The percentage of the second component is calculated by subtracting the first value from 100%.

The following formula is applied:

t°m: Is the average minimum temperature for the last 15 days, measured in Celsius degrees. Only use values under 0° C.

h°m: Is the average minimum relative humidity for the last 15 days, expressed as a percentage t°hm: Is the historical minimum temperature in Celsius degrees h°hm: Is the historical minimum relative humidity, expressed as a percentage F: Is the Filo Index $$F = \frac{t°m \times h°m}{t°hm \times h°hm}$$

With the Filo Index, the % of Component No. 1 (% C1) is calculated in the following way:

50×$F$=% C1

The percentage of the Component No. 2 (% C2) can be obtained as follows:

100−% C1=% C2

The optimum time in which the product should be applied over the crops should be more than 7 days prior to a forecasted frost. The application can be achieved through a spray hose or by any adequate method of pulverizing, depending on the quantity of crops to be covered. The process must guarantee a uniform spray over all the plants. Previously installed sprinkler irrigation systems may be used for the product application, method that protects crops against frost that wastes natural resources that are running out, such as water. The protection achieved by use of the composition of the present invention will last between 20 to 30 days in the absence of rain or until it rains.

From the time at which the product is applied over the crops, the process requires a week in order to achieve the internal equilibrium of temperature and humidity of the plant to the environment, this establishes the dew point. It is therefore necessary to have the best forecast dates on which the frosts will occur in order to be able to apply the product beforehand and allow it to work properly.

The results for the component percentages will vary from 30 to 55% for each of the components. One must take into account that the necessary dilution of the concentrate and the dilution of drinking water will be necessary.

The other components of the composition are a bactericide and a fungicide. Because of the development stage at which the crops will be at the time of the frosts, these product applications will be important for the health of the plants. In this way we take advantage of the same application for all purposes.

Description of the novelty of the methodology of this invention in regards to Argentinian Patent No. AR075324A1 from the same inventor. By means of the product formulation and its application, the methodology produces equilibrium between the internal humidity of the plant and the humidity of the environment. This guarantees that freezing will occur outside of the plant's tissues (frost), avoiding the occurrence of freezing before condensation, which produces the freeze of the water contained inside of the plant tissues with the corresponding damage to the tissues. As previously indicated, some of the components are known, for example, to modify the freezing point of mixtures. This is not the innovation since this function is not what produces the protection. What is unprecedented is the method in which the composition is used (which is very sensitive to the variations of the percentages of the components of the mixture). After many trial-and-errors we have achieved an optimization of the method, putting into practice what was known in theory.

As previously mentioned, small variations in the percentages of the components of the mixture produce effects contrary to those desired. Based on data obtained through experiments conducted jointly with the National Institute of Argentina Technology (INTA) in the Mendoza Province of Argentina, a variable index was obtained as a function of the temperature and the humidity of the different application zones that allowed us to optimize the methodology to be applied. This methodology produced very good results in accordance to the tests realized in Alto Valle during a first stage of joint work.

As discussed, this invention specifically provides a composition that acts on the equilibrium of the humidity between the plant and the environment, establishing outside the plant tissues the necessary condensation to allow freezing to occur outside of the plant without damage to the plant's tissues. The composition acts by taking water from the plant or from the environment. Therefore, it is very important to carefully dossifying the components of the mixture in order to avoid obtaining effects contrary to those desired. For this is what the Filo Index is used for.

The application of the product over the crops is achieved through a spray hose or by whatever means is adequate to pulverize the mixture, depending on the quantity of plants to be protected. During this procedure, a uniform spray over all the plants must be achieved. Installed sprinkler systems can be used for this purpose. The protection gained through the application of this invention will last for 20 to 30 days or until it rains (whichever happens first).

Utilizing the Filo Index (real temperature and humidity/historical values for the area) and the knowledge of when the frost will occur, the time of application of the product is determined as well as the percentages of each component that must be used in the formula in order to obtain the desired results. These percentages vary from 20% to 65% volume for each of the components. At the same time, one must consider the necessary dilution of the concentrate. This dilution is done with water.

The remaining components, a bactericide and a fungicide, are added because of the development stage at which the plants are at the time of the frosts. These products are important for the health of the plants.

Description of the composition: the mixture contains alcohols and pharmacopoeia grade glycols, nipagin-nipasol, chloride benzalkonium, and food colorants.

Alcohols:

The alcohol used is 1,2,3 propanetriol, regarded as non-toxic and biodegradable in aqueous solution. Within the composition, the alcohol regulates the stability of the mixture and, depending on its concentration, changes the balance of moisture in its application, allowing us to obtain the expected results. In the formula, from 20% to 65% volume is used.

Glycols:

Glycols used is 1,2 propanediol. According to tests performed on animals, it has low toxicity and good biodegradability. Within the composition, glycols regulate the intervention of the alcohols so that, in case it becomes necessary, it can absorb moisture from the plant or from the environment. In the formula, from 20% to 65% volume is used.

Nipagin-Nipasol:

The methylparaben is the bactericide and the propylparaben is the fungicide. Both are easily biodegradable. Within the composition, they act as bactericides and fungicides. In the formula 0.1% volume of the final concentration is used.

Benzalkonium Chloride:

n-alkyl methyl benzyl ammonium chloride is used. It is a bactericide and an inhibitor of viral activity. It is biodegradable. In the current composition, as a bactericide, a 0.05% volume of the final concentration is used.

Colorant:

A bright blue dye and tartazine may be used.

Example of Product Use:

The following test results were presented to the National Institute of Agricultural Technology (INTA) of Argentina. INTA is a governmental agency of the Ministry of Agriculture, Livestock and Fisheries of Argentina.

Effects of the field application of an organic composition for black frost protection of crops and the method for its application in cherry (cv Lapins) and apple trees.

2012-13 Season

Alto Valle Test

Design and Application

The test was carried out in the EEA of INTA Alto Valle, located in the town of Cte. Guerrico, on an orchard of cv. Lapins cherries. On Sep. 12, 2012, three agreed treatments were applied: 10% composition, 20% composition and a 0% composition control group. Eight trees were sprinkled for each sample. A spray hose with four tanks and an engine was used. We worked at a pressure of 200 psi and the application volume was calculated by the TRV method, applying 1 l/10.67 m$^3$ of treetop (FIG. 1).

FIG. 1 shows the application of the composition by means of a spray hose.

INTA-EEA Alto Valle, September 2012.

Sampling and Laboratory Determinations

Figure 2:
FIG. 2 shows the conditioning of floral organs in the laboratory.

After 1, 5, and 8 days after the product application, 50 organ samples (darts or flowers) were obtained for each of the dates. Samples were taken to the laboratory where they were conditioned and placed on tergo pol trays. (FIG. 2). Subsequently, the organ samples were subjected to a controlled thermal descent of 2° C. per hour that reached a minimum temperature of −2.75° C. The behavior of the product composition was evaluated 24 hours later, as a function of the presence of necrotic tissue produced by the frost.

FIG. 2 shows the conditioning of the floral organs in the laboratory. FIG. 2 shows the first sample of floral buds, one day after product application and subjected to sub-zero temperatures in the laboratory.

Figure 3:
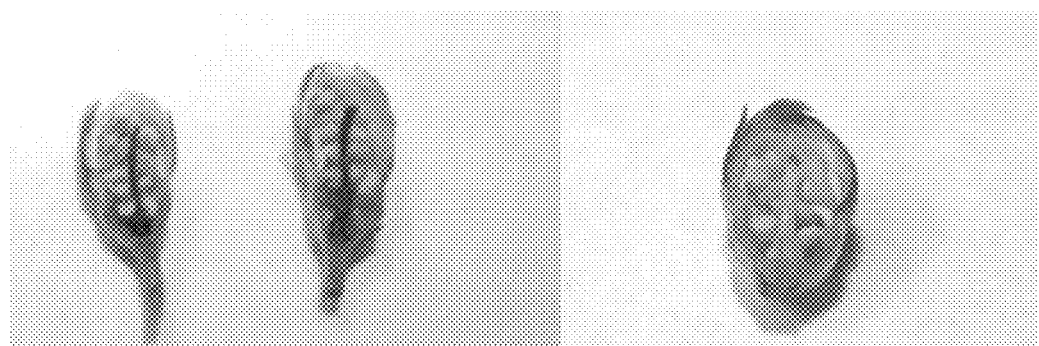
FIG. 3 shows on the left side two buds with necrotic stigmas, styles and ovaries; and on the right side, a healthy bud.

On the left hand side of FIG. 3, it shows two floral buds with necrotic stigmas, styles and ovaries. On the right hand side of FIG. 3, it shows a healthy bud.

After the controlled temperature descent performed in the laboratory over the floral buds collected after one day of the product application, it was observed that 50% of the samples presented damage in those buds treated with Antifresh, while the control group sample presented lesser damages (37%). In the samples obtained after five days of the product application, an even higher percentage of damaged organs were observed. This finding concurs with a higher susceptibility of tissues (Table 1).

Figure 4:
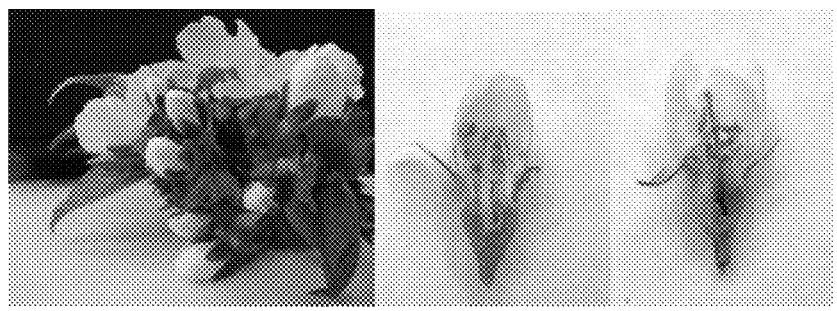
FIG. 4 shows a third sample taken 8 days after application of the product and subjected to temperatures of −2.7° C.

Conspicuously, in the sampling performed after 8 days of the product application, the percentages of damaged organs were lower than the previous date, despite being phenologically more advanced and therefore more susceptible to cold damage (FIG. 4). This could correspond to a better performance of the product on the whole plant through the course of the days. This is an interesting finding to be further evaluated.

Table 1. Displays the percentage of organs with frost damage for the three treatments: 0% composition (control group), 10% composition and 20% composition, after 1, 5 and 8 days after applying the product.

TABLE 1

| Treatment | Days after Application | | |
|---|---|---|---|
| | 1 | 5 | 8 |
| Control group | 37% | 67% | 51% |
| 10% Composition | 50% | 95% | 50% |
| 20% Composition | 50% | 100% | 26% |

FIG. 4 shows a third sampling obtained 8 days after product application and subjected to temperatures of −2.7° C.

Field Sampling:

On Sep. 25, 2012 a frost occurred that reached −2.3° C. for a period of 2 hours. On that morning, 80-60 flower samples were obtained for each treatment and by visual observation, the presence of necrotic tissue was determined and percentages were calculated. A lower percentage of damaged organs were observed for the 20% treatment, while no differences were observed between the Control Group and the 10% treatment. (Table 2).

Table 2 shows the percentage of cv Lapins cherry blossoms with necrotic tissues for the three treatments.

TABLE 2

| Treatment | % flowers with frost damage |
|---|---|
| Control Group | 11.6 |
| Composition: 10% | 12.0 |
| Composition: 20% | 2.5 |

2) Pomona Test

This field test was carried out in the village of Pomona over apple trees. In the orchard, three rows were used as a control sample (without treatment); three rows were sprayed with the product in two dosages, 10% and 20%.

The first application occurred on Sep. 20, 2012 as a function of a forecast that predicted the occurrence of temperatures of −2° C. Later, a second application was performed on Oct. 1, 2012, (10 days after the first application).

A data logger and sensors belonging to the company were left in place.

No sub-zero temperatures were registered in the rows tested and therefore, no samples were collected in order to evaluate damages. We did perform a visual observation of the general state of the plants after the second application in order to evaluate symptoms of phytotoxicity. We only observed a darker coloration on the plants treated with the product, with an oily appearance (FIG. 5).

Figure 5:
FIG. 5 shows a tree treated with the composition.

FIG. 5 shows a general view of a tree treated with the composition.

What is claimed is:

1. An organic composition for protecting crops against a black frost comprising:
   20% to 65% volume of 1,2,3 propanetriol;
   20% to 65% volume of 1,2 propanediol;
   methyl paraben;
   propylparaben;
   benzalkonium chloride; and
   a colorant;
   wherein the percentages of the components are calculated according to a formula:

% of 1,2,3 propanetriol=50×$F$

% of 1,2 propanediol=100−% of 1,2,3 propanetriol where:

$$F = \frac{t°m \times h°m}{t°hm \times h°hm}$$

wherein:
   t°m: is an average minimum temperature for the last 15 days, measured in Celsius degrees, only using values under 0° C.;
   h°m: is an average minimum relative humidity for the last 15 days expressed as a percentage;
   t°hm: is a historical minimum temperature in Celsius degrees;
   k°hm: is a historical minimum relative humidity expressed as a percentage;
   F: is a filo index;
   wherein the organic composition is adapted to be applied over the crops.

2. The organic composition according to claim 1, wherein the organic composition contains between 30% to 50% of 1,2,3 propanetriol and between 30% to 50% of 1,2-propanediol.

3. An organic composition for protecting crops against a black frost consisting of:
   20% to 65% volume of 1,2,3 propanetriol;
   20% to 65% volume of 1,2 propanediol;
   methyl paraben;
   propylparaben;
   benzalkonium chloride; and
   a colorant;
   wherein the percentages of the components are calculated according to a formula:

% of 1,2,3 propanetriol=50×$F$

% of 1,2 propanediol=100−% of 1,2,3 propanetriol where:

$$F = \frac{t°m \times h°m}{t°hm \times h°hm}$$

wherein:
t°m: is an average minimum temperature for the last 15 days, measured in Celsius degrees, only using values under 0° C.;
h°m: is an average minimum relative humidity for the last 15 days expressed as a percentage;
t°hm: is a historical minimum temperature in Celsius degrees;
h°hm: is a historical minimum relative humidity expressed as a percentage;
F: is a filo index;
wherein the organic composition is adapted to be applied over the crops.

\* \* \* \* \*